(12) United States Patent
Shanks et al.

(10) Patent No.: US 6,474,535 B1
(45) Date of Patent: Nov. 5, 2002

(54) WELDING METHOD AND APPARATUS

(75) Inventors: Charles Shanks, Schaumburg, IL (US); Kevin Helle, Bartlett, IL (US); John Krewer, Palatine, IL (US); Robert Hallgren, Lakemoor, IL (US)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/601,962

(22) PCT Filed: Nov. 19, 1999

(86) PCT No.: PCT/GB99/03884

§ 371 (c)(1),
(2), (4) Date: Oct. 6, 2000

(87) PCT Pub. No.: WO00/30803

PCT Pub. Date: Jun. 2, 2000

Related U.S. Application Data (60) Provisional application No. 60/109,214, filed on Nov. 20, 1998.

(30) Foreign Application Priority Data

Dec. 2, 1998 (GB) ............................................. 9826526

(51) Int. Cl.[7] ................................................. B21D 39/00
(52) U.S. Cl. ...................... 228/164; 228/60; 228/173.4; 228/212
(58) Field of Search .............................. 228/164, 141.1, 228/135, 137, 212, 173.1, 173.4, 60, 101, 173.5; 600/1–8; 29/592

(56) References Cited

U.S. PATENT DOCUMENTS

| | | | | |
|---|---|---|---|---|
| 3,715,799 A | * | 2/1973 | Flood et al. | 29/475 |
| 4,011,370 A | * | 3/1977 | Eckerbom | 429/140 |
| 4,204,378 A | * | 5/1980 | Thompson | 53/403 |
| 4,205,216 A | * | 5/1980 | Douglas | 219/121 L |
| 4,323,055 A | * | 4/1982 | Kubiatowicz | 128/1.2 |
| 4,580,715 A | * | 4/1986 | Schalch | 228/144 |
| 4,702,228 A | * | 10/1987 | Russell, Jr. et al. | 128/1.2 |
| 4,727,233 A | * | 2/1988 | Pavese et al. | 219/121 PK |
| 4,857,260 A | * | 8/1989 | Schoenig, Jr. et al. | 376/245 |
| 4,976,912 A | * | 12/1990 | Madle et al. | 376/249 |
| 4,991,765 A | * | 2/1991 | Sugiyama | 228/164 |
| 5,137,204 A | * | 8/1992 | Compagnucci | 228/173.4 |
| 5,342,283 A | * | 8/1994 | Good | 600/8 |
| 5,375,756 A | * | 12/1994 | Haughton et al. | 228/10 |
| 5,405,309 A | * | 4/1995 | Carden, Jr. | 600/3 |
| 5,609,291 A | * | 3/1997 | Hummel | 228/212 |
| 5,713,828 A | * | 2/1998 | Coniglione | 600/7 |
| 5,807,231 A | * | 9/1998 | Liprie | 600/3 |
| 5,990,441 A | * | 11/1999 | Zaenglein et al. | 219/78.16 |
| 5,997,463 A | * | 12/1999 | Cutrer | 600/8 |

* cited by examiner

*Primary Examiner*—M. Alexandra Elve
*Assistant Examiner*—Zidia Pittman
(74) *Attorney, Agent, or Firm*—Robert F. Chisholm; Royal N. Ronning, Jr.

(57) ABSTRACT

In a method for welding closed one end of each of a multiplicity of open-ended tubes suitable for use as brachytherapy capsules (100), each tube is loaded into a holder (52), brought to a welding station (80), has one end welded closed and is then released from the holder (52). A number of holders can 2 be arranged on the periphery of a rotatable member (50), each holder being loaded with a tube at a first station, and then carrying the tube to a welding station (80) and an ejection station (90). The tubes can be loaded into the holders individually by means of an escapement mechanism (40). The invention also extends to apparatus for carrying out the method.

22 Claims, 6 Drawing Sheets

WELDING METHOD AND APPARATUS

This application claims the benefit of provisional application No. 60/109,214 filed on Nov. 20, 1998.

The present invention relates to a welding method and apparatus, and more particularly to a method and apparatus for automated welding of tubes for use in brachytherapy.

In the treatment of various cancers, and in particular prostate cancer, a process called brachytherapy has proved effective. In brachytherapy, small capsules containing radioactive material are implanted in or near to the tumour.

Figure 7:
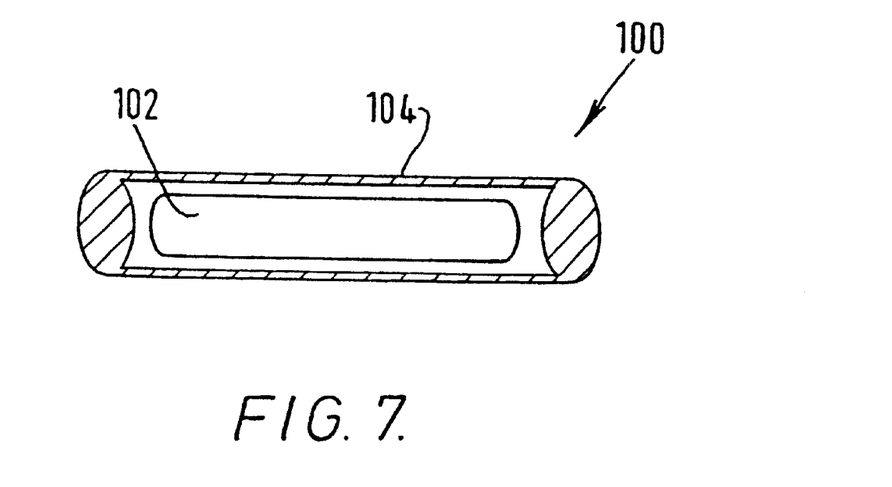
FIG. 7 is a cross-sectional view of a brachytherapy capsule or seed.

One known form of capsule or canister, commonly used to treat prostate cancer and referred to as a "seed", is shown in FIG. 7. The capsule 100 comprises a silver rod 102, coated with a radioactive isotope of iodine such as I-125, inside a hollow titanium tube 104. The ends of the tube are welded closed. Resin balls coated with radioactive iodine can be used instead of the silver rod 102. The completed capsule has a width of approximately 1.0 mm and a length of approximately 4.5 mm. The capsules or seeds can be implanted into a patient individually; alternatively, the capsules can be inserted into medical stitching material or suture, which is then inserted into the prostate and left there.

The number of capsules implanted into each patient obviously varies in accordance with the regime of treatment required, but is commonly in the region of 50 to 100. The capsules are normally made by hand, with the welding process used to close the ends of the tube being carried out manually. It will be appreciated that making such a large number of capsules for each patient by hand takes considerable time and expense.

According to a first aspect of the invention, there is provided an automated method of welding closed one end of each of a multiplicity of open-ended tubes suitable for use in the manufacture of brachytherapy capsules, which comprises repeating the steps of loading each tube into a holder, bringing the tube in the holder to a welding station, welding closed one end of the tube, and releasing the welded tube from the holder.

With such a method, a large number of tubes can be processed relatively quickly.

Preferably, the step of loading each tube into a holder comprises the steps of orientating the tubes into a particular orientation in a feeder, and feeding each tube from the feeder to a holder. Once orientated in the feeder, the tubes can be fed to the holder in a desired orientation. Manual picking up and orientation of the tubes is avoided.

As the tubes are for use in making brachytherapy seeds, they will be of a suitable size for brachytherapy implantation, for example, a few millimetres long by about one millimetre wide. The tubes are typically a little longer than the product brachytherapy seed, since it is usual for some of the tube material to be used to form the weld closure.

The welding of one end of the tube closed is preferably effected by melting the material of the tube such that the melted material forms the end closure. Preferably, no additional material is required.

Closure of the remaining open end of the tube will be effected after the active substance for brachytherapy has been inserted.

In general, the tubes to be welded will be formed by being cut from a long length of tubing, and having been so cut they will be randomly orientated. According to the method of the invention, the tubes are orientated in the feeder, so that each tube is ready to be fed to a holder. A preferred method comprises agitating the tubes in order to orientate them in the feeder.

Various ways may be used to control feeding of each tube to a holder. For example each tube may be individually picked up by a robot arm and placed in the holder. Preferably, the method comprises arranging the tubes end to end one above another in the feeder, urging a restraining member against a side of the lowermost-but-one tube to prevent it from downward movement, and releasing the lowermost tube from the feeder individually to the holder. The restraining member thus engages the lowermost-but-one tube and in so doing all the tubes above are held in position, allowing the lowermost tube to be individually released. After release, a blocking member is preferably moved into a blocking position below the tubes and the restraining member is retracted to allow the tubes to drop down, the then lowermost tube being stopped by the blocking member. The restraining member can then be advanced against the now lowermost-but-one tube and the feeding cycle is then repeated.

In a preferred method, the holder receives a tube, conveys the tube to the welding station, and releases the tube, said holder moving in a closed loop.

The provision of a holder which moves in a closed loop facilitates the automation of the welding process. The tube to be welded is supplied to the holder in a particular orientation. The tube is then carried to the welding station where it is welded. The welded tube is released, preferably at an ejection station to which it is carried from the welding station. Since the holder moves in a closed loop, it comes back to its original position, and the procedure can then be repeated.

It is possible to use one holder, although the rate of production of such an apparatus is low, as it can only operate on a single tube at a time. Accordingly, it is preferred that a plurality of said holders are provided. This allows greater productivity.

The welding of the end of each tube obviously requires high temperatures in order to melt the metal of the tube. It is possible for these high temperatures to cause damage to whatever is holding the tube during the welding operation, particularly if repeated welding operations are carried out. Some form of cooling can be provided to reduce the risk of damage. However, in a preferred method, the holders move through said welding station sequentially, each of the plurality of holders cooling between successive welding operations while the other holders move through the welding station. This ensures that after each of the holders holds a tube while it is being welded, it cools down before it next holds a tube being welded. This reduces the risk of heat damage to the holders.

Many possible methods of moving the or each holder through the welding station can be employed. For example, each could be individually driven along a track. However, in a preferred method, the or each holder is mounted at the periphery of a rotatable member. Receiving, welding and releasing stations may conveniently be provided at successive points along the rotational path of the holder. Where a plurality of holders are provided they can all be mounted by the rotatable member, with the advantage of simplicity, as it is then only necessary to provide a single drive means.

The holder may for example be a cavity into which the tube can be dropped by the feeder and which restricts movement of the tube adequately during welding. Preferably, however, the holder adopts an open condition when receiving and releasing a tube and a closed condition to grip the tube firmly at least during welding of the tube. This arrangement assists the receiving and releasing steps, whilst properly holding the tube during welding.

The holder may be in the closed condition at all times except when receiving and releasing a tube. However, the method preferably comprises causing the holder to move from the open condition to the closed condition when the holder is at the welding station. Thus, means can be provided at the welding station for causing the closing action, rather than such means being provided as part of the holder itself. This can advantageously simplify the design of the holder, which is particularly advantageous where the holder is conveyed from one processing station to another, e.g. by a rotatable member.

Viewed from another aspect the invention provides an automated method of welding closed one end of each of a multiplicity of open-ended tubes suitable for use as brachytherapy capsules, comprising repeating the steps of feeding each individual tube to a holder in an open condition, conveying the holder in the open condition to a welding station, causing the holder to close and grip the tube firmly by means of a holder actuator provided at the welding station, and welding one end of the tube closed. The holder actuator is advantageously not conveyed with the holder but instead is provided at a fixed location at the welding station.

The holder may have a floor portion for preventing downward movement of the tube during conveyance. However, this is not necessary and the method preferably comprises sliding the tube on a slide plate during conveyance of the holder. It has been found, contrary to expectations, that the lower ends of the tubes are not damaged as a result of sliding along the slide plate.

Thus, as long as the tubes are of uniform lengths, the top end of the tube will always be the same height above the slide plate. Provided the welder is also fixed in position, the distance between the upper end of the tube and the welding unit will remain constant. This can ensure that the tube is in the correct position for welding. Thus it is strongly preferred that the multiplicity of tubes for use in the preferred embodiment of the present invention are of uniform length.

It is possible for the welded tubes (also referred to as "cans") to be removed from the holders by being picked out, either by hand or by providing a further piece of apparatus to carry out this step. However, it is preferred that the slide plate be provided with a cut-out region, allowing cans to fall past the slide plate. The cans are then removed from the holders by the force of gravity. A preferred method therefore comprises conveying the welded tube to a release position where the slide plate is provided with a cut-out region, allowing the can to fall through the cut-out region.

The holder can take a number of forms, as long as the tube is held correctly. For example, the tube could be held in an inflatable collar, which is normally deflated and can be inflated when it is necessary to hold the tube tightly. However, it is preferred that said holder is in the form of a pair of jaws which are biassed to an open position and can be selectively closed. This allows the tube to be inserted into the holder when they are in their open position, where the spacing between the jaws is relatively wide, and so facilitates insertion of the tube. This also allows for release of the tube by opening the jaws.

It is possible for the jaws themselves to be provided with means allowing them to be closed tightly around the tube. For example, a solenoid or a pneumatic cylinder could have its ends attached to the halves of the jaw, and would then be able to open or close the jaws e.g. at the welding station. However, as described above, a holder actuator is preferably provided at the welding station to close the jaws. This simplifies the construction of the jaws, and, where a plurality of sets of jaws are provided, involves the provision of just one holder actuator, rather than one for each set of jaws.

In a preferred method, the holder is in the form of a block slidably mounted in a recess in a holder support, said block being biassed outwardly by resilient means, e.g. compression springs, retained between said block and said holder support. This arrangement has the advantage that the holder can be closed tightly by pushing the block against the resilient bias, and this can be done by means such as a solenoid or an air cylinder.

Preferably, the block is retained on the holder support by bolts passing through the block and engaging in the holder support, the block being biassed outwardly by the resilient means, and the bolts retaining the block on the holder support against the resilient bias and thus serving to define the open condition of the block, which can be varied by tightening or loosening the bolts. When the block is in its open position, it is biassed away from the recess, and so the distance between the block and the recess is a maximum. This is the position where the tube will preferably be loosely held in the holder. The bolts can be tightened or loosened to change this spacing, for example to accommodate thicker or thinner tubes, which may be needed to make different types of capsule.

The spacing between the block and the recess is important, as it must be large enough to allow the tube to easily enter the holder, but sufficiently small to ensure that the tube is held as required. In particular, the tube must be held in such a way as to ensure that when the holder is closed tightly around it, it is in the correct position for welding. The spacing can be set by inserting a gauge member of known thickness into the gap and tightening the bolts until the jaws just contact the gauge member, but this is an awkward procedure and does not guarantee that the bolts will not be over tightened. Accordingly, it is preferred that a set screw is provided in said recess, said set screw defining a point beyond which said bolts may not be tightened. This ensures that the spacing of the block and the recess is set correctly.

Provision of the set screw to ensure correct spacing of the block and the recess is also considered to be of inventive merit, and so according to a further aspect of the invention there is provided an automated method of welding closed one end of each of a multiplicity of open-ended tubes suitable for use as brachytherapy capsules, comprising repeating the steps of receiving a tube in a holder mounted on a holder support, conveying the tube past a welding station where one end of the tube is welded closed in a welding operation, and releasing the welded tube, said holder being in the form of a block slidably mounted in a recess on the holder support and retained on said holder support by bolts passing-through said block and engaging in said holder support, said block being biassed outwardly by resilient means acting between said block and said holder support, said bolts retaining said block on the holder support against the resilient bias and thus serving to define an open condition of the block, said open condition of said block being variable by means of tightening or loosening said bolts, and wherein a set screw is provided in said recess to define a point beyond which said bolts may not be tightened.

Since the holder will hold the tube while it is being welded, it is necessary for the holder to be formed from a material which has sufficient heat-resistance. It is preferred that the or each holder is formed from Elkonite. This material, an alloy of tungsten and copper, has good heat-resistance, but is easier to work than tungsten itself.

It is also preferred that the holder support, e.g. rotatable member, is formed from Elkonite.

The invention also extends to apparatus for carrying out the methods for welding closed one end of each of a multiplicity of tubes for use as brachytherapy capsules as described above.

A preferred embodiment of the invention will now be provided by way of example only and with reference to the accompanying drawings, in which.

Figure 1:
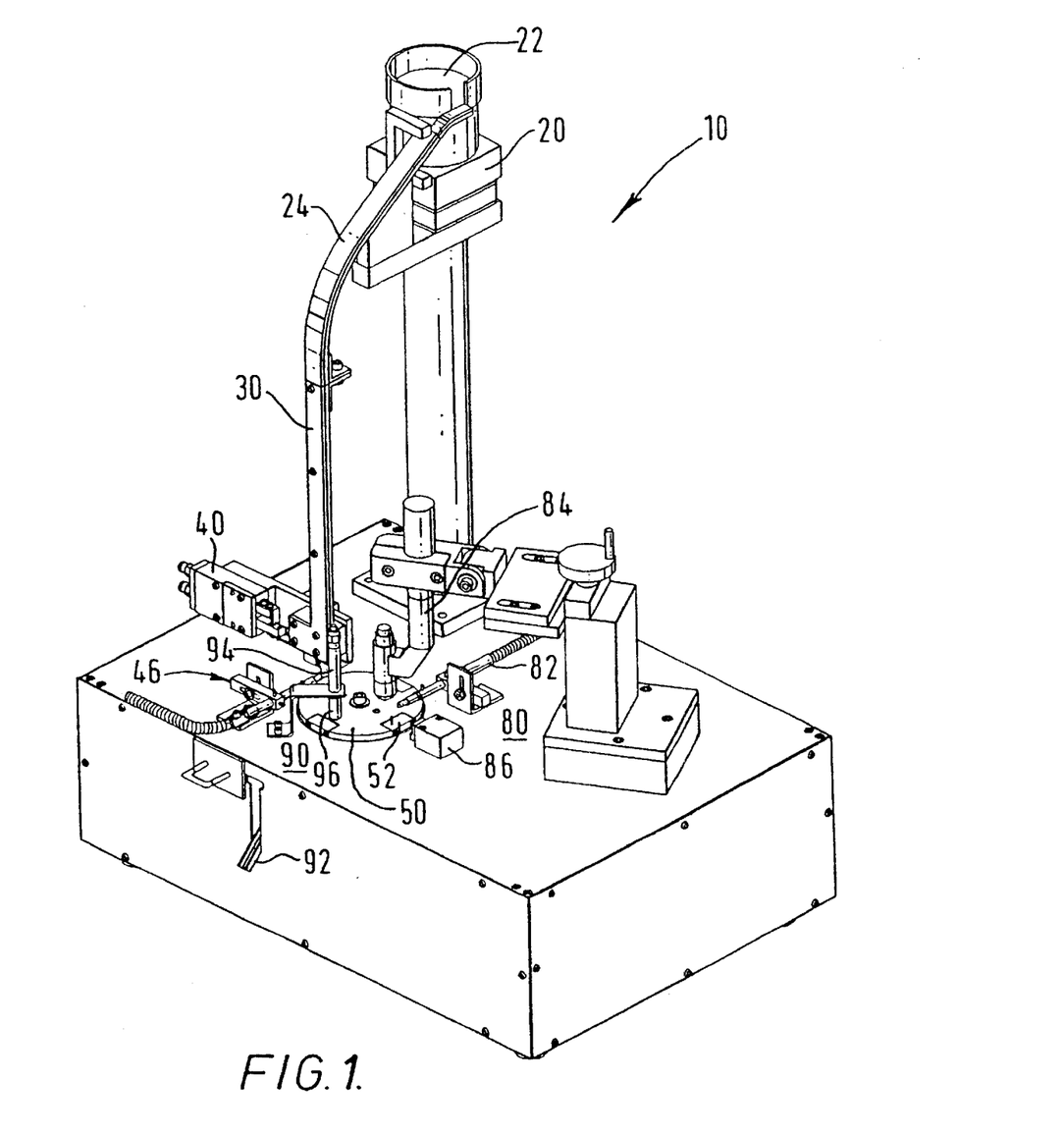
FIG. 1 is an overall perspective view of the preferred embodiment of the automated tube welder.

FIG. 1 shows a general perspective view of the preferred embodiment of the automated tube welder 10. The titanium tubes which are used to form the capsules have a width of around 1.0 mm and a length of around 6.5 mm. The tubes arrive in a bowl 22 of a vibrating hopper 20. The vibration of the hopper serves to orientate the tubes, and they pass into a gravity feed line 30. The tubes pass through to the lower end of the gravity feed line, where they are stopped by an escapement assembly 40. The escapement assembly 40 allows only one tube through at a time, and retains the remaining tubes in a vertical stack in the feed line. The tube released by the escapement assembly falls into a jaw 52 of a generally circular turret assembly 50. The turret 50 has four circumferentially equispaced jaws 52, each of which can hold one tube, and the turret 50 is rotated to move the tube sequentially through a number of operating stations. The first station is the one where the tube is received by the jaws. The turret is then rotated by 90° twice, to bring the tube to a welding station 80 incorporating a welding unit 84. A sensor 82 is located at or near the welding station, and as the turret rotates the sensor detects the presence or absence of a tube sticking up from the turret. The welding unit is only operated if the presence of the tube has been detected by the sensor assembly; if a tube is detected, then the upper end of the tube is welded closed by the welding unit. Once the welding process is started, it follows a preset welding program, which ends with a signal being sent back indicating that the welding process is complete. If the welding program is started and the weld sequence is not completed, the process will terminate with a weld error signal. If, on the other hand, no tube is detected, then the welding unit is not activated. The turret 50 is then rotated by a further 90° to bring the welded tube or can to an ejection station 90, where it is ejected. The operation of the automated tube welder 10 is controlled by a control unit, which in the preferred embodiment is an Allen Bradley PLC 5/11 programmable logic controller, using RS Logix software from Allen Bradley.

The various parts of the tube welder will now be described in greater detail.

The bowl 22 of the vibrating hopper 20 receives the tubes, and delivers them lengthwise down an exit chute 24. The width of the chute 24 is such that only one tube can pass down the chute at a time. This is achieved by having the diameter of the chute slightly greater than the diameter of the tubes (which is approximately 1 mm) but substantially less than the length of the tubes (which is around 6.5 mm), so that an in-line arrangement of the tubes results. Hoppers of this type are available from Service Engineering Inc., and the hopper will not be described further.

Figure 2:
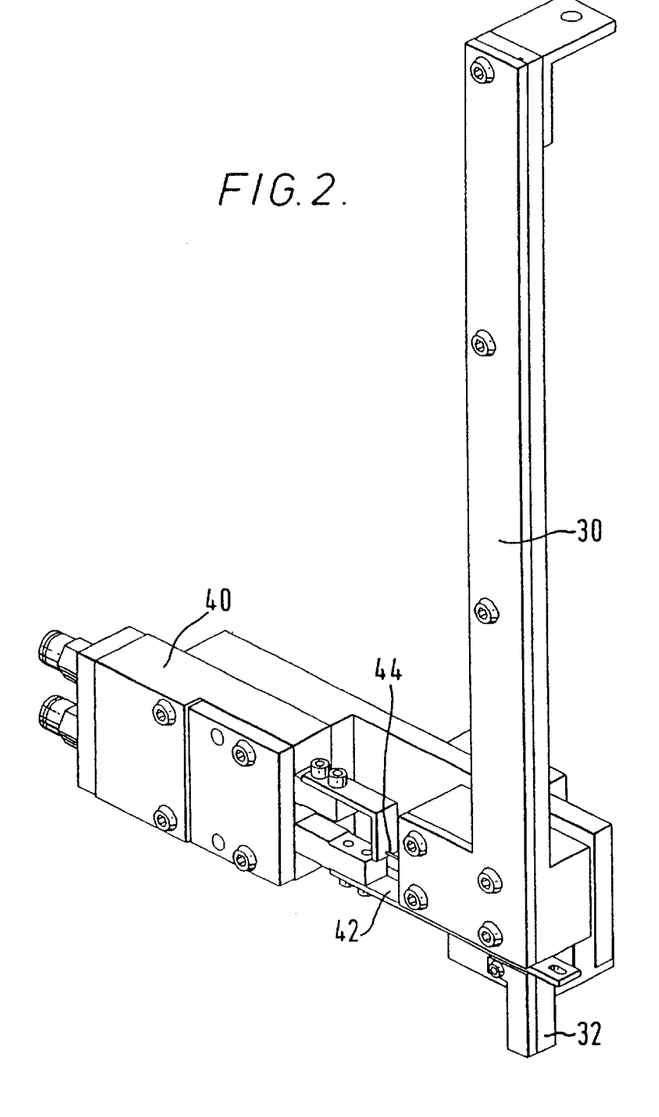
FIG. 2 is an enlarged perspective view of the feed line and the escapement assembly.

The upper end of the gravity feed line 30 is attached to the lower end of the exit chute 24, and the tubes leave the exit chute 24 and enter the feed line 30 under gravity. The width of the feed line 30 is similar to that of the chute 24, so that only one tube can pass down the feed line at any one time. The tubes thus form a vertical column in the feed line, stacked end to end.

In addition, the inner surfaces of the chute and the feed line are formed to be as smooth as possible. This reduces the friction between the tubes and the chute and feed line, and so reduces the chance of the tubes jamming during feeding.

Figure 3:
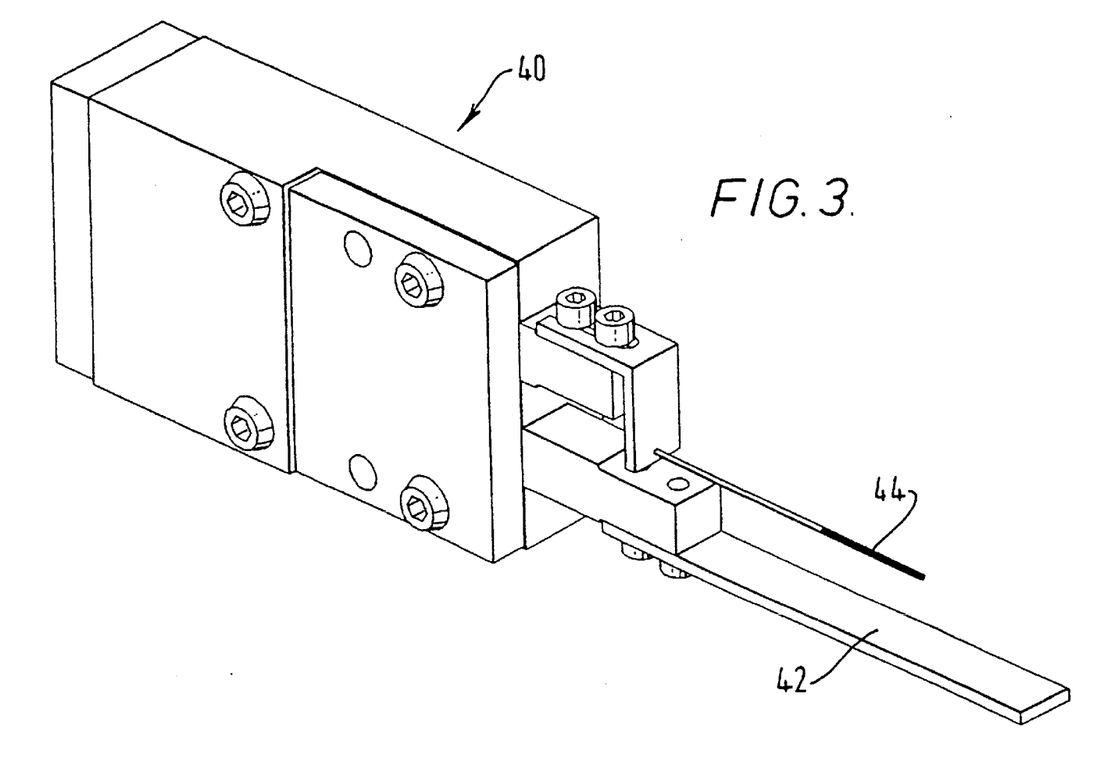
FIG. 3 is a perspective view of the escapement assembly.

At the lower end of the feed line 30 is the escapement assembly 40, which ensures that the tubes leave the feed line one by one. The escapement assembly includes a plate 42, which normally blocks the passage of tubes from the feed line 30, such that the lowermost tube rests on the plate 42. The escapement assembly also includes a resilient member 44, which normally urges the tube just above the lowermost tube against the side of the feed line 30, with sufficient force to prevent this tube from moving downwards when the tube below it moves, but not so much force that the tube will be damaged.

It will be appreciated that the walls of the tubes are very thin, so as to minimize any attenuation of the radiation from the radioisotope such as radioactive iodine, and it is preferred that the walls have a thickness of around 0.05 mm. Excessive force can damage the tubes, by crushing the walls towards each other, and this is obviously undesirable. For this reason, the resilient member is preferably in the form of a spring which is easily compressed.

The plate 42 and the resilient member 44 are moved by air cylinders, controlled by the control unit.

In operation, the escapement assembly 40 will normally have the plate 42 positioned so as to block the passage of tubes from the end of the feed line 30. The stack of tubes will thus be supported on the plate. The resilient member 44 then presses the lowermost-but-one tube against the side of the feed line 30, to prevent it from moving. The plate 42 is then moved to allow the lowermost tube to fall. It is possible for the plate to be formed with an opening which is brought into and out of registration with the opening at the bottom of the feed line, but it is preferred for the entire plate to be moved out of the way, to ensure that the lowermost tube is reliably dropped.

When the plate 42 is moved to allow the lowermost tube to drop from the feed line, it will be appreciated that the weight of all of the other tubes in the stack is supported by the tube which is pressed against the wall of the feed line 30 by the resilient member 44. However, since each tube has a very low mass (of the order of 10 mg), the total mass which must be supported in this way is relatively small.

The plate 42 is then returned to its original position, and the resilient member 44 is withdrawn. This allows the entire stack of tubes to drop down, so that they are again supported on the plate 42. Each time this cycle is repeated, one tube is allowed to drop from the bottom of the feed line 30. The operation of the escapement assembly 40 is controlled by the control unit. In addition, an interlock in the escapement 40 prevents both the plate 42 and the resilient member 44 allowing the tubes to pass at the same time.

Directly below the plate 42 of the escapement assembly 40, there is a funnel member 32. The funnel has a passage therethrough to allow a tube to pass down it. The purpose of the funnel is to ensure that the tube which is allowed out of the feed line 30 by the escapement assembly 40 is directed accurately, rather than simply allowed to fall. This is important, as if the tube were to simply be dropped from a height above the jaws 52 of the turret assembly 50, it could tumble out of its vertical orientation and as a result may not be properly received by the jaws 52.

In addition, a sensor unit 46 detects the presence of each tube as it passes through the escapement assembly 40. If the sensor fails to detect any tubes passing through the escapement assembly for a certain period of time during the operation of the apparatus, then an error message is generated by the control unit, and the user is informed of the location of the problem. The most likely causes for the error message being generated are that the tubes have jammed somewhere in the feed line 30 or that there are no tubes remaining in the hopper 20. In either case, it is necessary for the operator of the apparatus to intervene.

Figure 4:
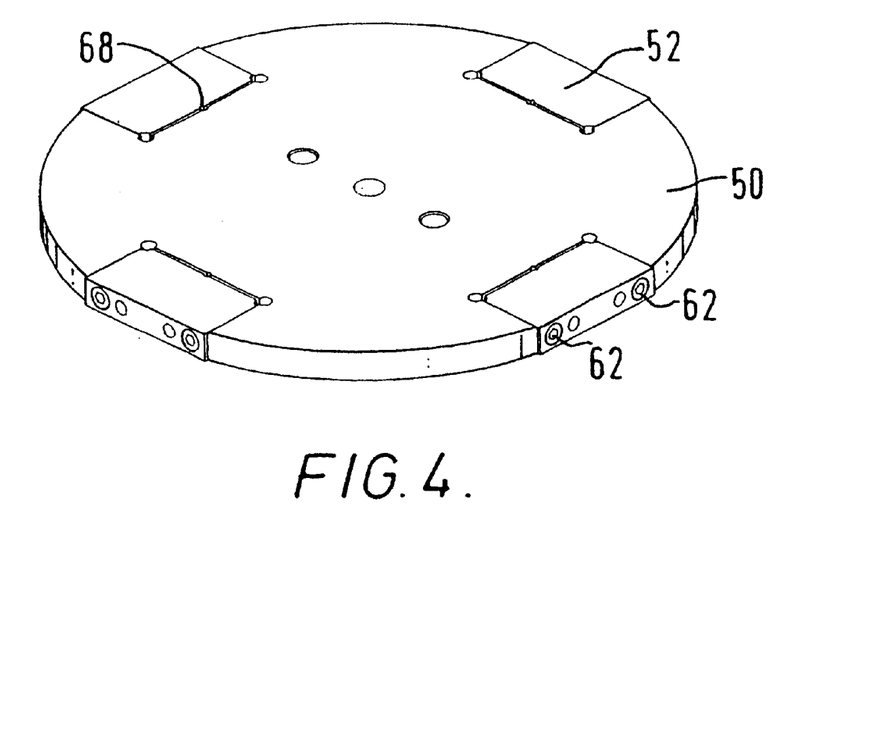
FIG. 4 is a perspective view of the turret.

As mentioned above, each tube that drops from the feed line 30 falls into a set of jaws 52 mounted on the turret assembly 50. There are four such sets of jaws 52, equispaced around the circumference of the turret 50. The turret itself is formed from a flat generally circular plate 54, rotatably mounted and driven by an indexing motor in such a way that it rotates in steps of 90°. The plate is made of a tungsten/copper alloy called Elkonite, which has a higher melting point than titanium. This is vital because a defined region of each titanium tube has to be at least partially melted during the welding process to form the weld, which involves relatively high temperatures. It is possible to form the turret from tungsten, rather than an alloy thereof, but tungsten is brittle and difficult to work, and thus forming the turret from tungsten presents a number of difficulties. In addition, Elkonite has the desirable property of heating up slowly but cooling quickly.

Figure 6:
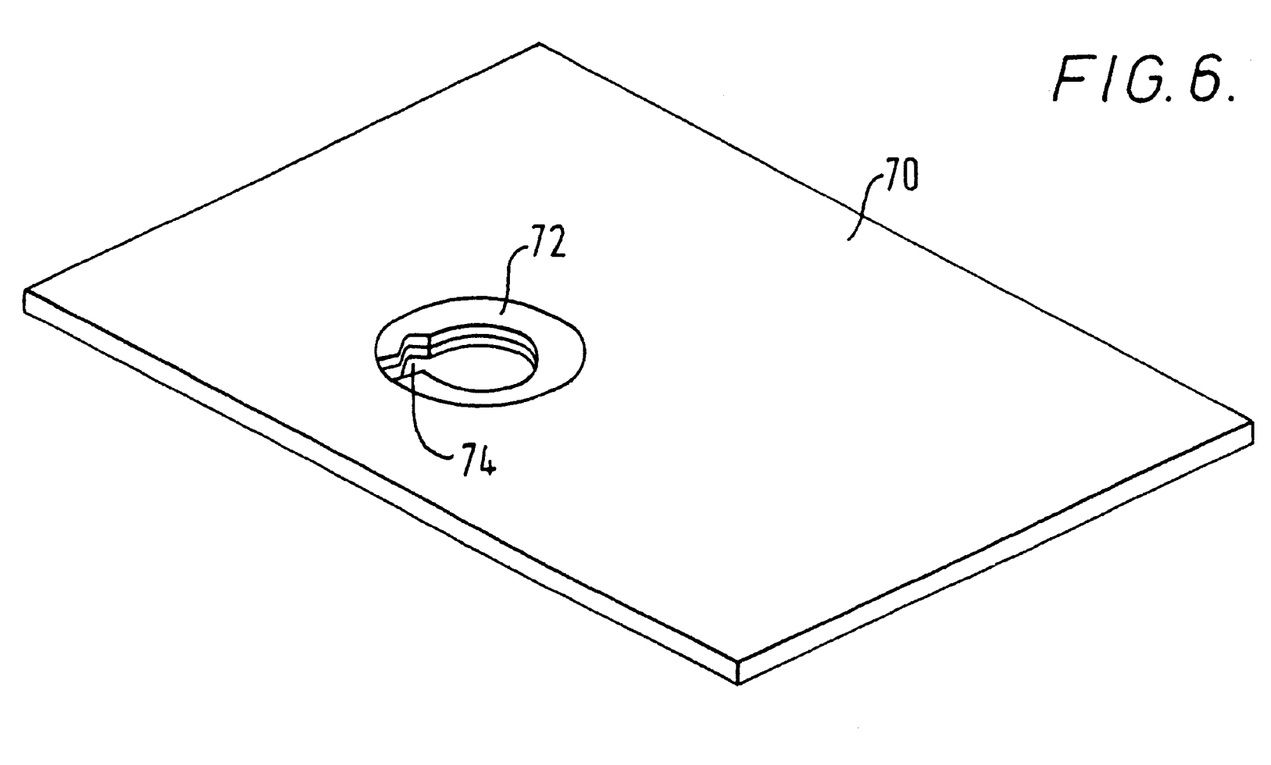
FIG. 6 is a perspective view of the table plate and slide plate.

The turret 50 is rotatably positioned above a table plate 70, shown in FIG. 6. It will be seen from this Figure that the central region of the table plate 70 over which the turret 50 rotates is removed, to allow the shaft of the indexing motor to pass through the table plate 70 and be attached to the turret 50 in order to drive it. In addition, the part of the table plate over which the turret 50 rotates is formed as a recess which accommodates a slide plate 72. The slide plate is formed of a material which has good wear resistance and good sliding qualities, and in the preferred embodiment is formed of aluminium bronze. The slide plate and the portion of the table plate 70 which it overlies are continuous around most of their circumferential extent, hut have a cut-out region 74 in one portion. The purpose of this cut-out region will be described later.

Figure 5:
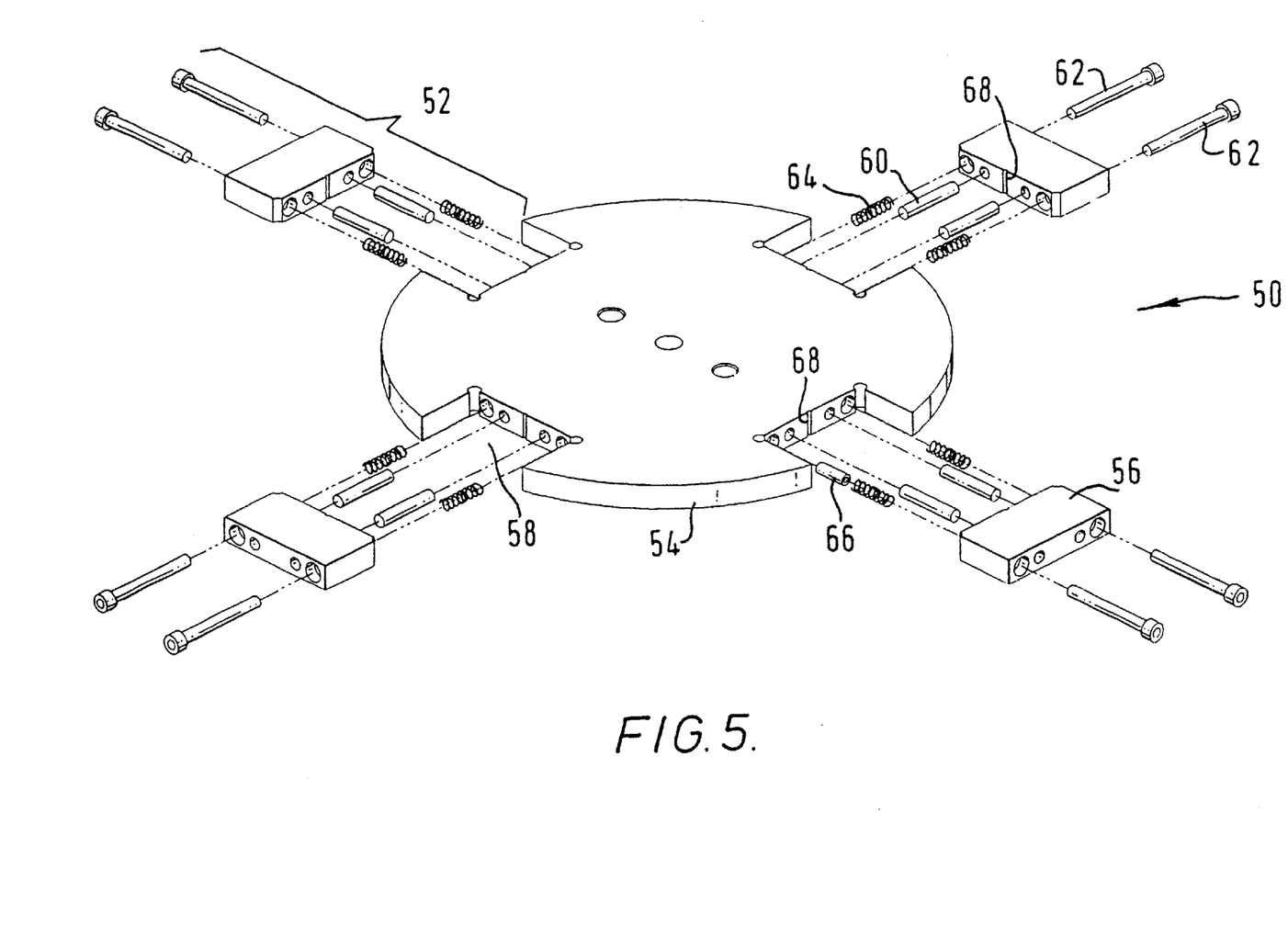
FIG. 5 is an enlarged exploded perspective view of the turret.

Each set of jaws 52 comprises a block 56 which is accommodated in a recess 58 in the plate 54. As best shown in FIGS. 4 and 5, two sets of jaws 52 are positioned at the ends of a first diameter of the plate 54, and the other two sets are mounted at the ends of the diameter normal to the first diameter. Each block 56 is mounted on guide pins 60 so as to be slidable in the recess 58 towards and away from the centre of the plate along the diameter. The block 56 is held in place by two bolts 62 which extend through the block parallel to the diameter of the plate, and engage in holes formed in the plate. Springs 64 surround the bolts 62 and are positioned between the recess 58 and the block 56 to bias the block outwardly until the block comes into contact with the heads of the bolts.

The end of the block 56 which faces the recess 58, and the end of the recess 58 which faces the block 56, are spaced from each other, and the space between the end of the block and the end of the recess defines the region into which the tube falls. In order to adjust the size of the region into which the tube falls, the bolts 62 can be tightened against the springs 64 (to reduce the size of the region) or loosened, so that the springs 64 push the block outwardly (to increase the size of the region).

During the setting-up of the turret 50, the bolts 62 are tightened to set the width of the jaws 52. This can be done by putting a gauge member of known thickness into the jaws and tightening the jaws until they just contact the gauge. However, this is an awkward and inaccurate procedure. To ensure that the jaw spacing is set correctly, a set screw 66 is provided in the recess 58 to ensure that the bolts 62 cannot be tightened beyond a set position. However, the springs 64 and guide pins 60 are arranged so that the block 56 can still slide into the recess 58 beyond this point, to reduce the width of the jaws.

The ends of the block 56 and the recess 58 are both formed with a semicylindrical groove 68. The radius of the groove 68 is very slightly less than the radius of the tube. When the bolts 62 have been tightened as far as they can, the distance between the ends of the block 56 and the recess 58 is set to be around 0.5 mm, which is less than the thickness of a tube. However, a tube can be easily accommodated between the semicylindrical grooves 68, and indeed there is substantial play between the grooves 68 and the walls of the tube.

Rotation of the turret 50 brings the tube held in the jaws 52 firstly to a welding station 80, located 180° away from the escapement 40, and then to an ejection station 90 90° further on.

It will be noted that there is no station positioned at 90° from the escapement assembly. However, if the process requires, a station could be put here to carry out an optional step useful to prepare the tube for welding. For example, an air blast could be used to blow any debris away from the end of the tube.

The welding station 80 comprises a sensor 82, a welding unit 84, and a clamping air cylinder 86. The welding unit 84 comprises a plasma arc welding torch, in which argon is used as an inert gas. Supply of current and argon gas to the welding torch is regulated by the welder power supply. The position of the welding head 88 of the welding unit can be adjusted in all three dimensions to ensure that it is properly aligned with the upper end of the tube.

The sensor assembly 82 detects the presence or absence of a tube in the jaws 52 of the turret 50. An optical detection system is used, and a signal from the sensor 52 is passed to the control unit. If the sensor detects a tube, then the welding unit 84 welds the upper end of the tube closed. If no tube is detected, then the welder is not operated. Of course, the sensor 82 could be positioned at the previous (empty) station if desired.

The clamping air cylinder 86 serves to close the jaws 52 of the turret 50. The piston of the clamping air cylinder 86 can be operated to move horizontally towards the centre of the turret when a set of jaws 52 are positioned at the welding station 80. When the piston moves in this manner, it applies a force to the block 56, pushing it into the recess 58. This clamps the tube between the groove 68 in the block 56 and the groove 68 in the recess 58, and thus ensures that the tube is accurately positioned for welding. It also ensures that there is good contact between the tube and the jaws, which is necessary for successful welding. The operation of the clamping air cylinder 86 is controlled by the control unit.

It will be appreciated that since the faces of the block and recess come together after the block has travelled a very short distance into the recess, the block has limited travel. As a result, it is extremely unlikely that the tube will be crushed or otherwise damaged by the jaws while it is being held for welding.

A quarter of a revolution further on is the ejection station 90. This station is positioned adjacent the parts of the table plate 70 and slide plate 72 which have the cut-out region 74. As the turret 50 rotates, the welded tube or can is brought to a position above the cut-out region 74. Normally, since the can is only held loosely in the jaws 52, it will fall from the jaws 52 under the influence of gravity, and will pass through the cut-out region 74 and down a delivery chute 92 into a collection bin (not shown).

On occasion, the can does not fall from the jaws 52 under gravity when it is positioned above the cut-out region 74. For this reason, an ejection unit is provided, comprising a vertical air cylinder 94, with the piston of the air cylinder biassed into its uppermost position by means of a spring. An ejector block 96 is attached to the lower end of the piston. When air is supplied to the cylinder 94, the piston is pushed downwardly, and the lower surface of the ejector block 96 contacts the upper end of the can. This suffices to push the can downwardly out of the jaws 52 into the delivery chute 92, and ensures that the cans are reliably ejected. Supply of air to the cylinder 94 is regulated by the control unit.

Further, although not shown in the diagrams, the welder is entirely enclosed by a plastic safety cage. The safety cage reduces the risk of operator injury (whether through welder burns or through trapping a finger or similar between moving parts). Further, the safety cage allows excess argon to build up near the welder to improve welding. In addition, the safety cage protects the welding area from external air currents, and reduces the amount of airborne contaminants near the welder.

The safety cage is provided with doors, to allow access to the welder when necessary (for example, when charging the hopper 20 with tubes). The doors have switches, which pass a signal to the control unit indicating whether the doors are closed or not. For automatic operation of the welder, the doors must be closed.

The operation of the automated tube welder will now be described.

Tubes are placed into the bowl 22 of the vibratory hopper 20, and are delivered down the exit chute 24 into the gravity feed line 30. The tubes form a vertical stack, with the lowermost tube resting on the plate 42 of the escapement assembly 40. The turret 50 is positioned such that a set of jaws 52 is aligned beneath the bottom of the funnel 32 of the gravity feed line 30, to receive a tube therefrom, and is held stationary in that position. The block 56 of the jaws 52 is biassed outwardly by the springs 64, and so the space between the grooves 68 in the block 56 and the recess 58 is somewhat larger than the cross-section of the tube. This facilitates entry of the tube into the jaws 52.

The resilient member 44 of the escapement assembly 40 then urges the lowermost-but-one tube in the stack against the side of the feed line 30. The plate 42 of the escapement assembly 40 is then moved to allow the lowermost tube in the stack to fall through the funnel 32 into the jaws 52. The tube released in this way falls under gravity into the gap between the grooves 68 in the block 56 and the recess 58, until its lower end comes into contact with the slide plate 72 beneath the turret 50. The length of the tube is slightly greater than the thickness of the turret, and so the upper end of the tube stands proud of the turret.

The plate 42 of the escapement assembly 40 is then returned to its original position, and the resilient member 44 releases the tube which it was holding, which then drops down to rest on the plate 42.

The turret is then rotated by 90°. The tube is carried along with the jaws 52, and its lower end slides on the slide plate 72. The weight of the tube is sufficiently small for the lower end of the tube to avoid being damaged as it slides on the slide plate 72. As there is no station positioned 900 from the escapement, no operations are carried out on the tube at this stage in the process. In the meantime, while the turret 50 is stationary, the escapement assembly 40 is operated again, to drop a tube into the second set of jaws.

The turret 50 is again rotated by 90°. The first tube is brought to the welding station 80, where its presence is detected by the sensor 82. The second tube is moved to the empty station.

A signal that a tube is present is passed to the control unit, which then prepares the welding unit 84 to make a weld. At the welding station 80, the air cylinder 86 is activated by the control unit to clamp the first tube firmly in position in the jaws 52, and while it is held in this way its upper end is welded closed. Following welding, the pressure in the air cylinder 86 is released, and the jaws 52 spring back to their previous position. Of course, if no tube is present in the jaws 52 (as will occur in the stages before the first tube reaches the welding station 80) then the sensor 82 passes a signal to this effect to the control unit, and the welder is not activated.

It will be appreciated that during the welding of the upper end of the tube, it is important for the turret 50 to be held stationary, to ensure that the tube remains beneath the welder. During this stationary period, the escapement assembly 40 is operated again to drop a tube into the third set of jaws 52.

The turret is again rotated by 90°. The first tube, by now welded closed at one end, is brought to the ejection station 90, where it falls into the delivery chute 92, either under its own weight or after being tapped by the ejector block 96. The second tube is brought to the welding station 80, where its presence is detected, the jaws 52 are closed by the air cylinder 86 and the end of the second tube is welded closed. The third tube is carried along by the jaws 52 but nothing is done to it. The escapement assembly 40 is again operated while the turret 50 is stationary during the welding process to drop a tube into the fourth set of jaws 52.

The turret is again rotated by 90°. This brings the second tube to the ejection station 90, the third tube to the welding station 80, and the fourth tube to the empty station. The escapement assembly 40 is operated again to drop a tube into the original set of jaws 52, which are now empty.

The process then continues, with each tube being dropped into a set of jaws 52 and conveyed through the welding station 80, where one end of the tube is welded closed, to the ejection station 90, where it is ejected. The apparatus thus continuously and automatically welds closed one end of each of the titanium tubes.

The time taken to complete a weld is the critical time in the cycle, which determines how quickly the welder can operate. At present, completion of a weld takes approximately three seconds, and rotation of the turret by 90° takes roughly two seconds. Each 90° step delivers a welded tube to the ejection station 90, and the production rate is around 600 welded tubes or cans per hour.

It will be noted that, although the welding unit 84 is operated in each cycle, each set of jaws 52 only holds the tube being welded every fourth cycle. This allows the material forming the turret 50 to be less heat-resistant than would be necessary if it were always the same part holding the tube being welded. In particular, it allows the turret to be formed from a tungsten alloy rather than tungsten itself.

The welded titanium tubes or cans produced by this process are received in a collection bin. They are subjected to a visual inspection, and those that are acceptable are filled with the appropriate radioisotope such as silver rods or resin balls coated with radioactive iodine. The capsules then have their other end welded closed. At present, the inspection, insertion and welding steps are carried out manually. However, it will be appreciated that even if these steps are carried out manually, having the first end of the tube welded closed automatically significantly reduces the amount of work and time involved in the production of the capsules. In addition, the automated process produces more consistent results than the manual welding of cans.

What is claimed is:

1. An automated method of welding closed one end of each of a multiplicity of open-ended tubes suitable for use as brachytherapy capsules, which comprises repeating the steps of:
   loading a plurality of tubes into a feed line positioned in overlying registry with a tube holder, said feed line located at a loading position;
   loading one of said plurality of tubes into said holder positioned adjacent an outside edge of a rotatable platform;
   transporting said holder between said loading position and a welding position at a welding station, wherein said loading and welding positions are distinctly located;
   welding closed one end of the one of said plurality of tubes; and
   releasing the welded tube from the holder.

2. A method as claimed in claim 1, wherein the multiplicity of open-ended tubes are fed in a continuous stream from a feeder.

3. A method as claimed in claim 2, wherein the feeder supplies the tubes in a particular orientation to a holder.

4. A method as claimed in claim 3, comprising agitating the tubes in order to orientate them in the feeder.

5. A method as claimed in claim 2 comprising arranging the tubes end to end one above another in the feeder, urging a restraining member against a side lowermost-but-one tube to prevent it from downward movement, and releasing the lowermost tube from the feeder individually to the holder.

6. A method as claimed in claim 1, wherein the holder receives a tube, conveys the tube to the welding station where one end of the tube is welded, and releases the welded tube, said holder moving in a closed loop.

7. A method as claimed in claim 6, wherein a plurality of said holders are provided.

8. A method as claimed in claim 7, wherein said holders move through said welding station sequentially, each of said plurality of holders cooling between successive welding operations while the other holders move through said welding station.

9. A method as claimed in claim 1, wherein said holder is mounted at the periphery of a holder support in the form of a rotatable member.

10. A method as claimed in claim 1, wherein said holder adopts an open condition when receiving and releasing a tube and a closed condition to grip the tube firmly at least during welding of the tube.

11. A method as claimed in claim 10, comprising causing the holder to move from the open condition to the closed condition when the holder is at the welding station.

12. A method as claimed in claim 10 or 11, wherein said holder is in the form of a pair of jaws which are biased to an open position and can be selectively closed.

13. A method as claimed in claim 10, wherein said holder is in the form of a block slidably mounted in a recess in a holder support, said block being biased outwardly by resilient means retained between said block and said holder support.

14. A method as claimed in claim 13, wherein said block is retained on said holder support by bolts passing through said block and engaging in said holder support, the block being biased outwardly by the resilient means, and the bolts retaining the block on the holder support against the resilient bias and thus serving to define the open condition of the holder, which can be varied by tightening or loosening said bolts.

15. A method as claimed in claim 14, wherein a set screw is provided in said recess, said set screw defining a point beyond which said bolts may not be tightened.

16. An automated method of welding closed one end of each of a multiplicity of open-ended tubes suitable for use as brachytherapy capsules, comprising repeating the steps of feeding each individual tube to a holder in an open condition, conveying the holder in the open condition to a welding station, causing the holder to close and grip the tube firmly by means of a holder actuator provided at the welding station, and welding one end of the tube closed.

17. A method as claimed in claim 16, comprising sliding the tube on a slide plate during conveyance of the holder.

18. A method as claimed in claim 17, comprising conveying the welded tube to a release position where the slide plate is provided with a cut-out region, and allowing the tubes to fall through the cut-out region.

19. An automated method of welding closed one end of each of a multiplicity of open-ended tubes suitable for use as brachytherapy capsules, comprising repeating the steps of receiving a tube in a holder mounted on a holder support, conveying the tube past a welding station where one end of the tube is welded closed in a welding operation, and releasing the welded tube, said holder being in the form of a block slidably mounted in a recess on the holder support and retained on said holder support by bolts passing through said block and engaging in said holder support, said block being biased outwardly by resilient means acting between said block and said holder support, said bolts retaining said block on the holder support against the resilient bias and thus serving to define an open condition of the block, said open condition of said block being variable by means of tightening or loosening said bolts, and wherein a set screw is provided in said recess to define a point beyond which said bolts may not be tightened.

20. A method as claimed in claim 1, wherein the holder is formed from Elkonite.

21. A method as claimed in claim 1, wherein a holder support is formed from Elkonite.

22. Apparatus for carrying out a method as claimed in claim 19.

* * * * *